(12) United States Patent
Raymond et al.

(10) Patent No.: US 8,585,611 B1
(45) Date of Patent: Nov. 19, 2013

(54) SAFETY BLOOD COLLECTOR SYSTEM

(76) Inventors: Allen J. Raymond, New Port Richey, FL (US); Li Lin, Zhejiang (CN); Cai Long, Zhejiang (CN)

(*) Notice: Subject to any disclaimer, the term of this patent is extended or adjusted under 35 U.S.C. 154(b) by 0 days.

(21) Appl. No.: 13/566,257

(22) Filed: Aug. 3, 2012

(51) Int. Cl.
*A61B 5/00* (2006.01)
*B65D 81/00* (2006.01)
*A61M 5/32* (2006.01)

(52) U.S. Cl.
USPC .......................... 600/576; 604/195; 604/198

(58) Field of Classification Search
USPC .......................... 600/576–579; 604/192–198
See application file for complete search history.

(56) References Cited

U.S. PATENT DOCUMENTS

| | | | | | |
|---|---|---|---|---|---|
| 3,304,934 | A | * | 2/1967 | Bautista | 600/579 |
| 4,695,274 | A | * | 9/1987 | Fox | 604/198 |
| 4,743,233 | A | * | 5/1988 | Schneider | 604/192 |
| 4,774,964 | A | * | 10/1988 | Bonaldo | 600/576 |
| 4,790,827 | A | * | 12/1988 | Haber et al. | 604/198 |
| 4,846,808 | A | * | 7/1989 | Haber et al. | 604/195 |
| 4,892,107 | A | * | 1/1990 | Haber | 600/576 |
| 4,915,702 | A | * | 4/1990 | Haber | 604/198 |
| 5,070,885 | A | * | 12/1991 | Bonaldo | 600/576 |
| 5,120,311 | A | * | 6/1992 | Sagstetter et al. | 604/110 |
| 5,181,524 | A | * | 1/1993 | Wanderer et al. | 600/577 |
| 5,259,392 | A | * | 11/1993 | Schmitt | 600/576 |
| 5,337,756 | A | * | 8/1994 | Barbier et al. | 600/576 |
| 5,395,346 | A | * | 3/1995 | Maggioni | 604/195 |
| 5,498,244 | A | * | 3/1996 | Eck | 604/198 |
| 5,562,103 | A | * | 10/1996 | Sak | 600/576 |
| 5,709,669 | A | * | 1/1998 | Haining | 604/232 |
| 6,755,804 | B2 | * | 6/2004 | Crawford | 604/110 |
| 6,764,465 | B2 | * | 7/2004 | Chen | 604/110 |
| 2004/0143196 | A1 | * | 7/2004 | Chen | 600/576 |
| 2006/0074349 | A1 | * | 4/2006 | Fan | 600/576 |
| 2012/0259243 | A1 | * | 10/2012 | Shaw et al. | 600/576 |

* cited by examiner

*Primary Examiner* — Max Hindenburg
*Assistant Examiner* — John Pani

(57) ABSTRACT

A housing has upper, lower, and central sections having a common axis and forming an interior chamber. An opening in the intermediate section has upper, lower, and sides edges. A flap has one edge coupled with the opening and covers the opening. A support is slidable between extended and retracted orientations. The support has central, upper, and lower extents. A cylindrical bore extends through the support. The support has legs, including a short leg, extending downwardly and outwardly and adapted to be radially contracted with the short leg within the opening restrained from downward movement. The flap is adapted to be depressed to move the short leg from contact with the opening and spring the legs outwardly to move the support from the extended orientation to the retracted orientation. Upper and lower needles extend from the upper and lower extents of the support for movement therewith.

6 Claims, 3 Drawing Sheets

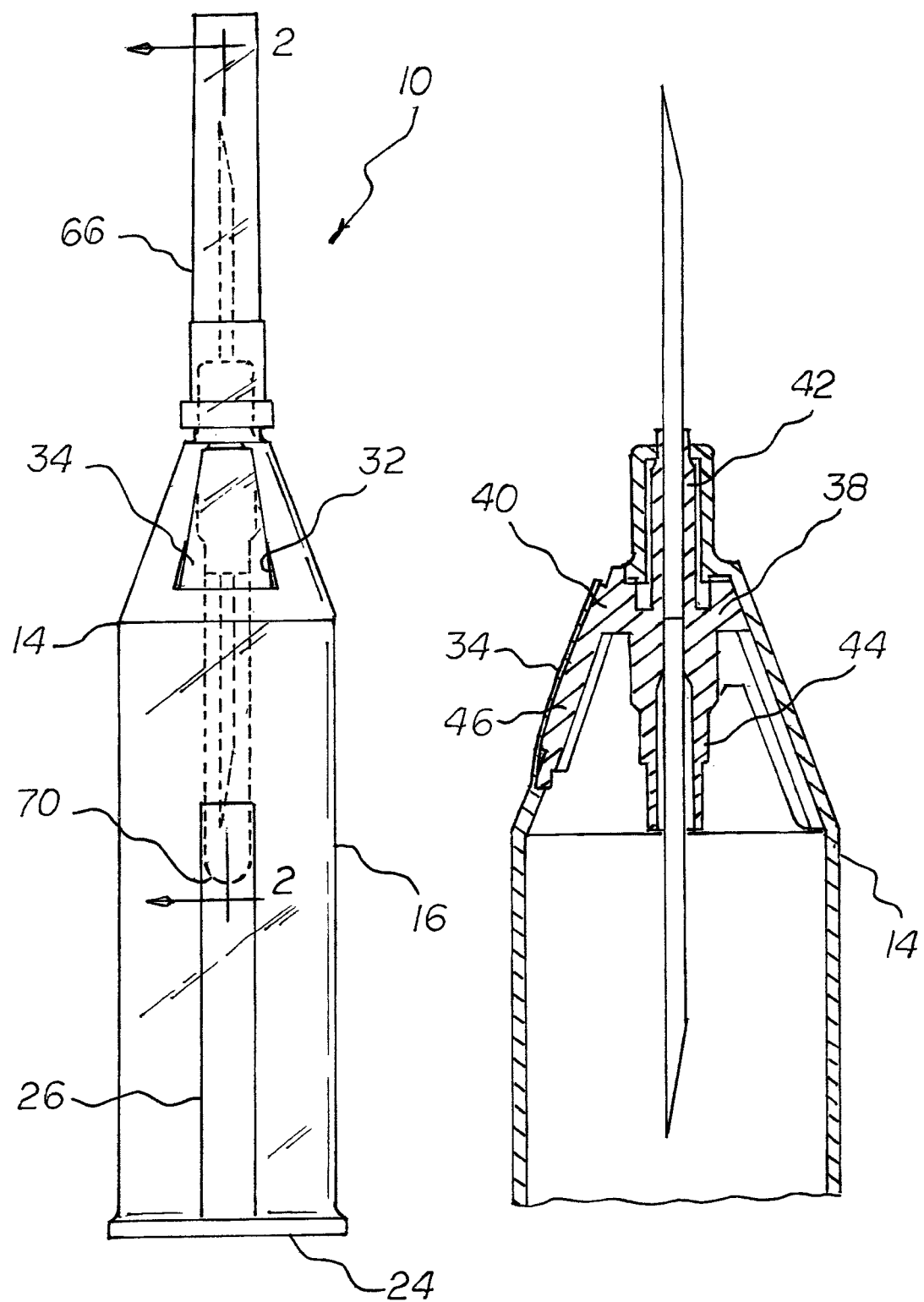

SAFETY BLOOD COLLECTOR SYSTEM

BACKGROUND OF THE INVENTION

Field of the Invention

The present invention relates to a safety blood collector system and more particularly pertains to drawing blood from a patient through a needle and thereafter retracting the needle for abating an unintended needle stick, the drawing of the blood and the retracting of the needle being done in a safe, convenient and economical manner.

SUMMARY OF THE INVENTION

In view of the disadvantages inherent in the known types of blood collection systems of known designs and configurations now present in the prior art, the present invention provides an improved safety blood collector system. As such, the general purpose of the present invention, which will be described subsequently in greater detail, is to provide a new and improved safety blood collector system and method which has all the advantages of the prior art and none of the disadvantages.

To attain this, the present invention essentially comprises a safety blood collector system. A housing has upper, lower, and central sections having a common axis and forming an interior chamber. An opening in the intermediate section has upper, lower, and sides edges. A flap has one edge coupled with the opening and covers the opening. A support is slidable between extended and retracted orientations. The support has central, upper, and lower extents. A cylindrical bore extends through the support. The support has legs, including a short leg, extending downwardly and outwardly and adapted to be radially contracted with the short leg within the opening restrained from downward movement. The flap is adapted to be depressed to move the short leg from contact with the opening and spring the legs outwardly to move the support from the extended orientation to the retracted orientation. Upper and lower needles extend from the upper and lower extents of the support for movement therewith.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved safety blood collector system which has all of the advantages of the prior art blood collection systems of known designs and configurations and none of the disadvantages.

It is another object of the present invention to provide a new and improved safety blood collector system which may be easily and efficiently manufactured and marketed.

It is further object of the present invention to provide a new and improved safety blood collector system which is of durable and reliable constructions.

An even further object of the present invention is to provide a new and improved safety blood collector system which is susceptible of a low cost of manufacture with regard to both materials and labor, and which accordingly is then susceptible of low prices of sale to the consuming public, thereby making such safety blood collector system economically available to the buying public.

Even still another object of the present invention is to provide a safety blood collector system for drawing blood from a patient through a needle and thereafter retracting the needle for abating an unintended needle stick, the drawing of the blood and the retracting of the needle being done in a safe, convenient and economical manner.

Lastly, it is an object of the present invention to provide a new and improved safety blood collector system for drawing blood from a patient through a needle and thereafter retracting the needle for abating an unintended needle stick, the drawings of the blood and the retracting of the needle being done in a safe, convenient and economical manner.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a front elevational view of a safety blood collector system constructed in accordance with the principles of the present invention.

FIG. 2 is a cross sectional view taken along line 2-2 of FIG. 1.

The same reference numerals refer to the same parts throughout the various Figures.

DESCRIPTION OF THE PREFERRED EMBODIMENT

Figure 3:
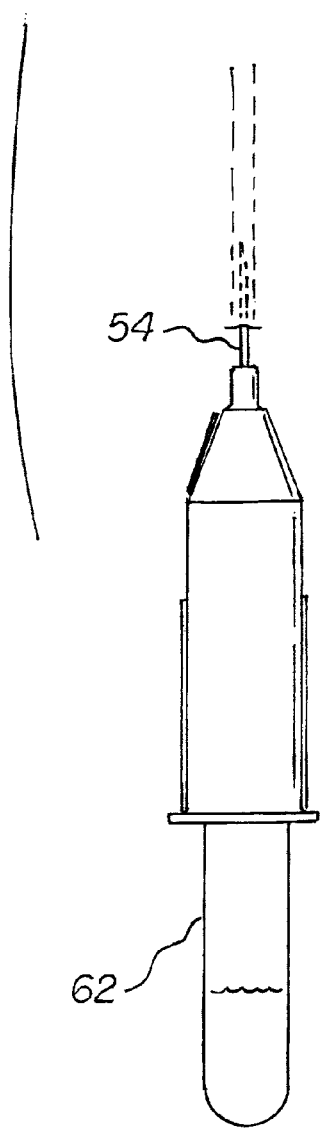
FIG. 3 is a front elevational view of the system during use while drawing blood.

With reference now to the drawings, and in particular to FIG. 1 thereof, the preferred embodiment of the new and improved safety blood collector system embodying the principles and concepts of the present invention and generally designated by the reference numeral 10 will be described.

The present invention, the safety blood collector system 10 is comprised of a plurality of components. Such components in their broadest context include a housing, a support, and upper and lower needles. Such components are individually configured and correlated with respect to each other so as to attain the desired objective.

First provided is a housing 14. The housing has a cylindrical lower section 16. The lower section has a first diameter. The housing has a cylindrical upper section 18. The upper section has a second diameter. The second diameter is less than the first diameter. The housing has a frusto-conical central section 20. The central section couples the upper and lower sections. The upper and lower and intermediate sections form an interior chamber. The upper and lower and intermediate sections have a common central axis. Each section has an axial length. The axial length is measured along the central axis. A plurality of annular rings 22 is provided. The annular rings are provided in the chamber. The annular rings extend inwardly at an intermediate extent of the lower section. An annular shoulder 24 is provided. The annular shoulder extends radially outwardly from a lowermost extent of the lower section. In this manner the lower section is supported and strengthened. An axial enlargement 26 is provided. The axial enlargement is provided vertically. The axial enlargement is provided in the lower section. The axial enlargement has a planar exterior surface for increased rigidity and indicia. The upper section has an aperture 28. The aperture is provided in an uppermost extent of the upper section. The aperture is provided coaxial with the central axis.

Figure 4:
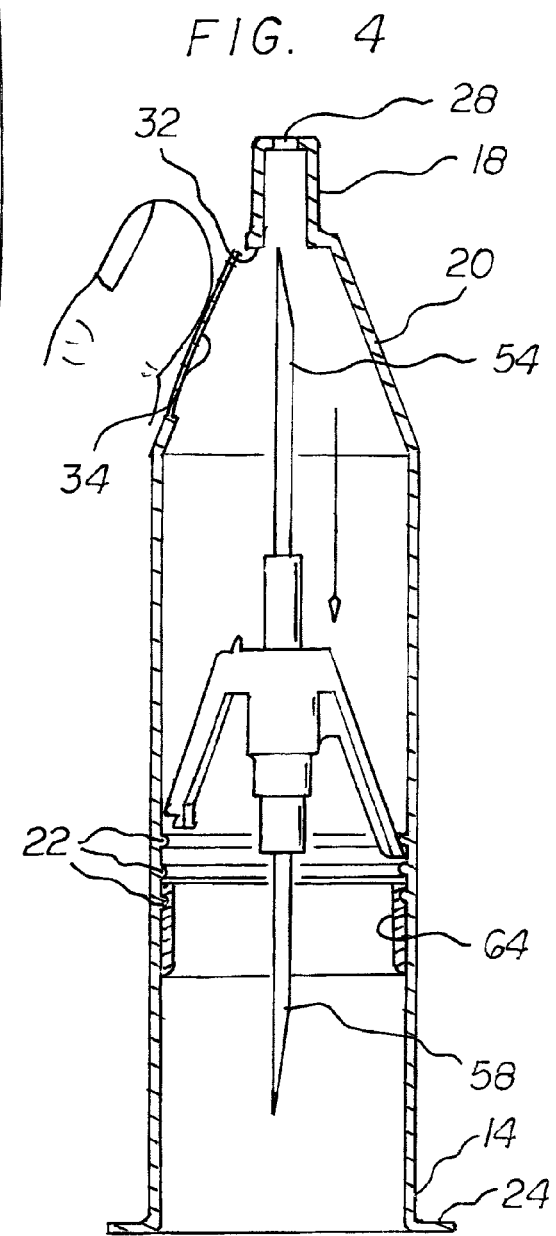
FIG. 4 is a cross sectional view of the system after use following needle withdrawal from a patient's arm and retraction of the needle into the housing.
Figure 5:
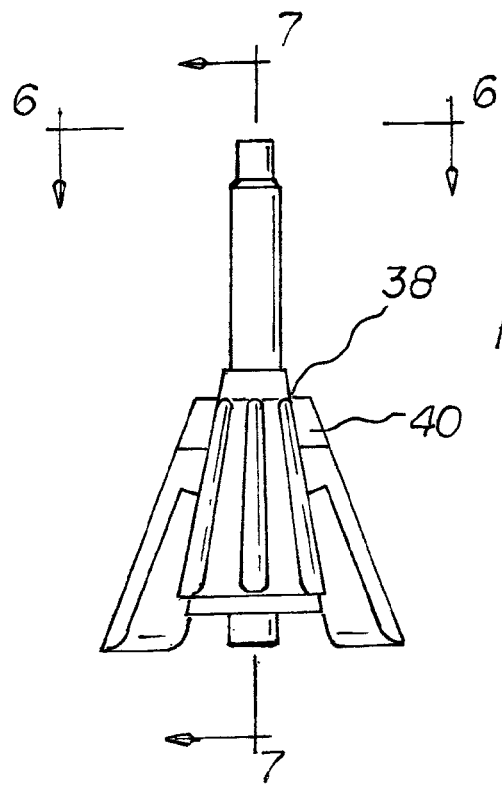
FIG. 5 is a front elevational view of the support shown in FIGS. 1, 2 and 4.
Figure 6:
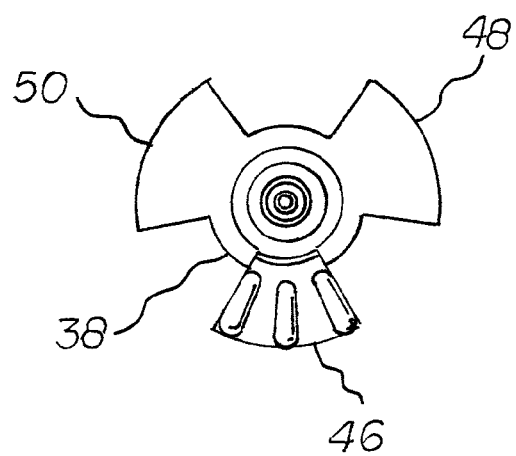
FIG. 6 is a plan view of the support taken along line 6-6 of FIG. 5.
Figure 7:
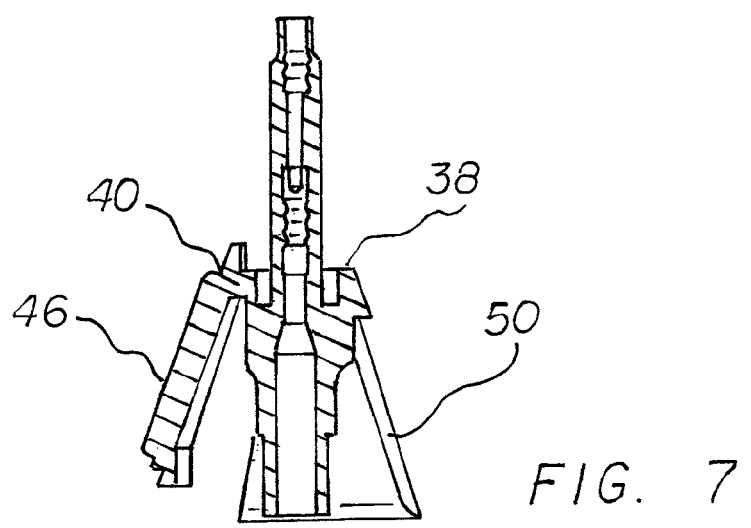
FIG. 7 is a cross sectional of the support taken along line 7-7 of FIG. 5.

The intermediate section has an opening 32. The opening is in a trapezoidal configuration. The opening has a shorter upper end. The shorter upper end is provided adjacent to the upper section. The opening has a longer lower end. The longer lower end is provided adjacent to the lower section. The opening has tapering sides. The upper and lower ends extend circumferentially for between 100 and 140 degrees. The upper and lower ends are axially spaced for between 70 and 95 percent of the axial length of the central section. A trapezoidal flap 34 is provided. The trapezoidal flap has an upper end. The trapezoidal flap has a lower end. The trapezoidal flap has tapering sides. The trapezoidal flap has a size and shape essentially equal to the size and shape to essentially cover the opening. The lower end of the flap is integrally formed with the lower end of the opening. In this manner the flap is movable by a user between a rest position and a depressed position within the chamber. In the rest position, the flap covers the opening. Note FIGS. 2 and 4. The housing, including the flap, is fabricated of a plastic material. The plastic material has limited flexibility and resilience.

A support 38 is provided. The support is located within the chamber. The support is slidable between an extended orientation and a retracted orientation. In the extended orientation, the support is provided above the lower section of the housing. In the retracted orientation. The support has a cylindrical central extent 40. The support has a cylindrical upper extent 42. The support also has a cylindrical lower extent 44. A cylindrical bore is provided. The cylindrical bore extends through the entire support. The support has three legs. The legs include one short leg 46 and two long legs 48, 50. Each of the legs extend downwardly and outwardly from the central extent. Each of the legs has a lower end. The lower end is normally spaced from the central axis a radial distance less than the radius of the lower section when the support is in the retracted orientation. The legs are adapted to be radially contracted with the short leg within the opening restrained from downward movement by contact with the lower edge of the opening when in the extended orientation. The flap is adapted to be depressed by a user. In this manner the short leg is moved from contact with the lower edge of the opening. In this manner the legs will spring outwardly. Also in this manner the support is moved from the extended orientation to the retracted orientation. Further in this manner both needles will be within the housing and needle stick will be abated. Note FIG. 4. The support includes the legs. The legs are fabricated of a plastic material. The plastic material has limited flexibility and resilience.

An upper needle 54 is provided. The upper needle has a lower end. The lower end is supported in the bore at the upper extent of the support. The upper needle has nan upper end for injection into a patient.

A lower needle 58 is provided. The lower needle has an upper end. The upper end of the lower needle is supported in the bore at the lower extent of the support. The lower needle has a lower end.

A blood collection tube 62 is provided next. The blood collection tube is removably positioned within the lower section of the housing. The blood collection tube has an elastomeric cover. The elastomeric cover is adapted to be pierced by the lower needle. In this manner the blood collecting tube may receive blood from a patient after passing through the upper and lower needles. A retainer ring 64 is provided. The retainer ring is secured within the housing. In this manner downward movement of the support is limited when moving from the extended to the retracted orientations.

Further provided is an upper cover 66. The upper cover is removably positioned over the upper needle. In this manner inadvertent needle stick is precluded.

Provided last is a lower cover 70. The lower cover is removably positioned over the lower needle. In this manner inadvertent needle stick is precluded.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A safety blood collector system comprising:
   a housing formed with cylindrical upper and lower sections and a frusto-conical central section, the sections having a common central axis and forming an interior chamber, an opening formed in the central section having upper and lower and sides edges, a flap covering the opening, the flap having one edge coupled with the opening;

a support located within the chamber and slidable between extended and retracted orientations, the support having central, upper and lower extents, a cylindrical bore extending through the support, the support being formed with legs including a short leg, each of the legs extending downwardly and outwardly, the legs adapted to be radially contracted with the short leg is within the opening and restrained from downward movement by contact with the lower edge of the opening, the flap adapted to be depressed to move the short leg from contact with the opening whereby the legs will spring outwardly to move the support from the extended orientation to the retracted orientation; and upper and lower needles extending from the upper and lower extents of the support for movement with the support.

2. The system as set forth in claim 1 wherein the housing and the support are fabricated of a plastic material with limited flexibility and resilience.

3. The system as set forth in claim 1 wherein the upper needle extends upwardly from the upper extent of the support and wherein the lower needle extends downwardly from the lower extent of the support and wherein both needles are totally within the chamber when in the retracted orientation.

4. The system as set forth in claim 1 and further including:
a blood collection tube removably positioned within the lower section of the housing, the blood collection tube having an elastomeric cover adapted to be pierced by the lower needle whereby the blood collecting tube may receive blood from a patient after passing through the upper and lower needles.

5. The system as set forth in claim 1 and further including:
a retainer ring secured within the housing to limit downward movement of the support when moving from the extended to the retracted orientations.

6. A safety blood collector system (10) for drawing blood from a patient through a needle and thereafter retracting the needle for abating an unintended needle stick, the system comprising, in combination:

a housing (14) formed to have a cylindrical lower section (16) with a first diameter, the housing having a cylindrical upper section (18) with a second diameter, the second diameter being less than the first diameter, the housing having a frusto-conical central section (20) coupling the upper and lower sections, the upper and lower and intermediate sections having a common central axis and forming an interior chamber, each section having an axial length measured along the central axis, a plurality of annular rings (22) formed in the chamber extending inwardly at an intermediate extent of the lower section, an annular shoulder (24) extending radially outwardly from a lowermost extent of the lower section for support and strengthening, an axial enlargement (26) vertically formed in the lower section with a planar exterior surface for increased rigidity and indicia, an aperture (28) formed in an uppermost extent of the upper section coaxial with the central axis;

an opening (32) formed in the intermediate section, the opening having a trapezoidal configuration, the opening having a shorter upper end adjacent to the upper section, the opening having a longer lower end adjacent to the lower section, the opening having tapering sides, the upper and lower ends extending circumferentially for between 100 and 140 degrees, the upper and lower ends being axially spaced for between 70 and 95 percent of the axial length of the central section, a trapezoidal flap (34) having an upper end and a lower end and tapering sides with a size and shape essentially equal to the size and shape to essentially cover the opening, the lower end of the flap being integrally formed with the lower end of the opening whereby the flap is movable by a user between a rest position covering the opening and a depressed position within the chamber, the housing including the flap being fabricated of a plastic material with limited flexibility and resilience;

a support (38) located within the chamber and slidable between an extended orientation above the lower section of the housing and a retracted orientation within the lower section of the housing, the support having a cylindrical central extent (40) with a cylindrical upper extent (42) and a cylindrical lower extent (44), a cylindrical bore extending through the support, the support being formed with three legs including one short leg (46) and two long legs (48), (50), each of the legs extending downwardly and outwardly from the central extent, each of the legs having a lower end normally spaced from the central axis a radial distance less than the radius of the lower section when the support is in the retracted orientation, the legs adapted to be radially contracted with the short leg is within the opening and restrained from downward movement by contact with the lower edge of the opening when in the extended orientation, the flap adapted to be depressed by a user to move the short leg from contact with the lower edge of the opening whereby the legs will spring outwardly to move the support from the extended orientation to the retracted orientation whereby both needles will be within the housing for abating needle stick, the support including the legs being fabricated of a plastic material with limited flexibility and resilience;

an upper needle (54) having a lower end supported in the bore at the upper extent of the support, the upper needle having an upper end for injection into a patient;

a lower needle (58) having an upper end supported in the bore at the lower extent of the support, the lower needle having a lower end;

a blood collection tube (62) removably positioned within the lower section of the housing, the blood collection tube having an elastomeric cover adapted to be pierced by the lower needle whereby the blood collecting tube may receive blood from a patient after passing through the upper and lower needles, a retainer ring (64) secured within the housing to limit downward movement of the support when moving from the extended to the retracted orientations;

an upper cover (66) removably positioned over the upper needle to preclude inadvertent needle stick; and a lower cover (70) removably positioned over the lower needle to preclude inadvertent needle stick.

* * * * *